(12) United States Patent
Behrends et al.

(10) Patent No.: US 6,376,547 B1
(45) Date of Patent: Apr. 23, 2002

(54) TUBERCULOCIDAL DISINFECTANT

(75) Inventors: Sabine Behrends, Pinneberg; Andreas Dettmann, Hamburg; Michael Mohr, Kaltenkirchen, all of (DE)

(73) Assignee: L'Air Liquide SANTE (International), Paris (FR)

( * ) Notice: Subject to any disclaimer, the term of this patent is extended or adjusted under 35 U.S.C. 154(b) by 0 days.

(21) Appl. No.: 09/231,632

(22) Filed: Jan. 15, 1999

(30) Foreign Application Priority Data

Jan. 15, 1998 (DE) .......................... 198 01 821

(51) Int. Cl.$^7$ .................. A61K 31/00; A61K 31/13; A01N 25/00
(52) U.S. Cl. .................. 514/579; 510/161; 510/131; 510/382; 510/384; 510/386; 424/405; 424/238; 424/409; 514/579; 514/663; 514/667; 514/670
(58) Field of Search .................. 510/161, 131, 510/382, 384, 386; 424/405, 238, 409; 514/579, 663, 667, 670

(56) References Cited

U.S. PATENT DOCUMENTS

| 4,128,662 A | 12/1978 | Lover et al. ................. 424/319 |
| 4,224,319 A | 9/1980 | Marcadet .................... 424/238 |
| 5,154,920 A | 10/1992 | Flesher et al. .............. 514/643 |

FOREIGN PATENT DOCUMENTS

| EP | 0 175 338 | 3/1986 |
| EP | 0 683 978 | 11/1995 |

OTHER PUBLICATIONS

Arshad et al. (CA 126:79917 abstract of GB 2298791), 1996.*
Block, S.S. "Disinfection, Sterilization and Preservation" 1991, Lea & Febiger, Philadelphia, Chapter 15: "Surface--active agents: amphoteric compounds", pp. 263–273.

* cited by examiner

*Primary Examiner*—Sabiha Qazi
(74) *Attorney, Agent, or Firm*—Young & Thompson

(57) ABSTRACT

The invention relates to the use of an N,N'-substituted glycine or of an N,N'-substituted derivative of glycine (a) of the general formula I

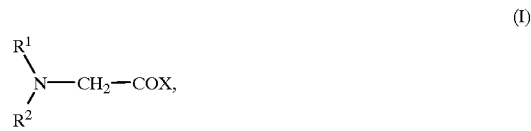

in which $R^1$ is hydrogen or a straight-chain or branched, saturated or unsaturated alkyl, alkaryl or aralkyl radical having 1 to 30 C atoms, which can optionally contain heteroatoms such as O, S and N, $R^2$ is a straight-chain or branched, saturated or unsaturated alkyl, alkaryl or aralkyl radical having 1 to 30 C atoms containing at least one primary, secondary or tertiary amino group and X is OH, $OR^3$, $NH_2$, $NHR^4$, $NR^4R^5$ or $O^-M^+$, where $R^3$, $R^4$ and $R^5$ are straight-chain or branched, saturated or unsaturated alkyl, alkaryl or aralkyl radicals which can be identical to or different from one another, and M is a metal cation, as active compound in a tuberculocidal disinfectant.

11 Claims, 1 Drawing Sheet

TUBERCULOCIDAL DISINFECTANT

FIELD OF THE INVENTION

Figure 1:
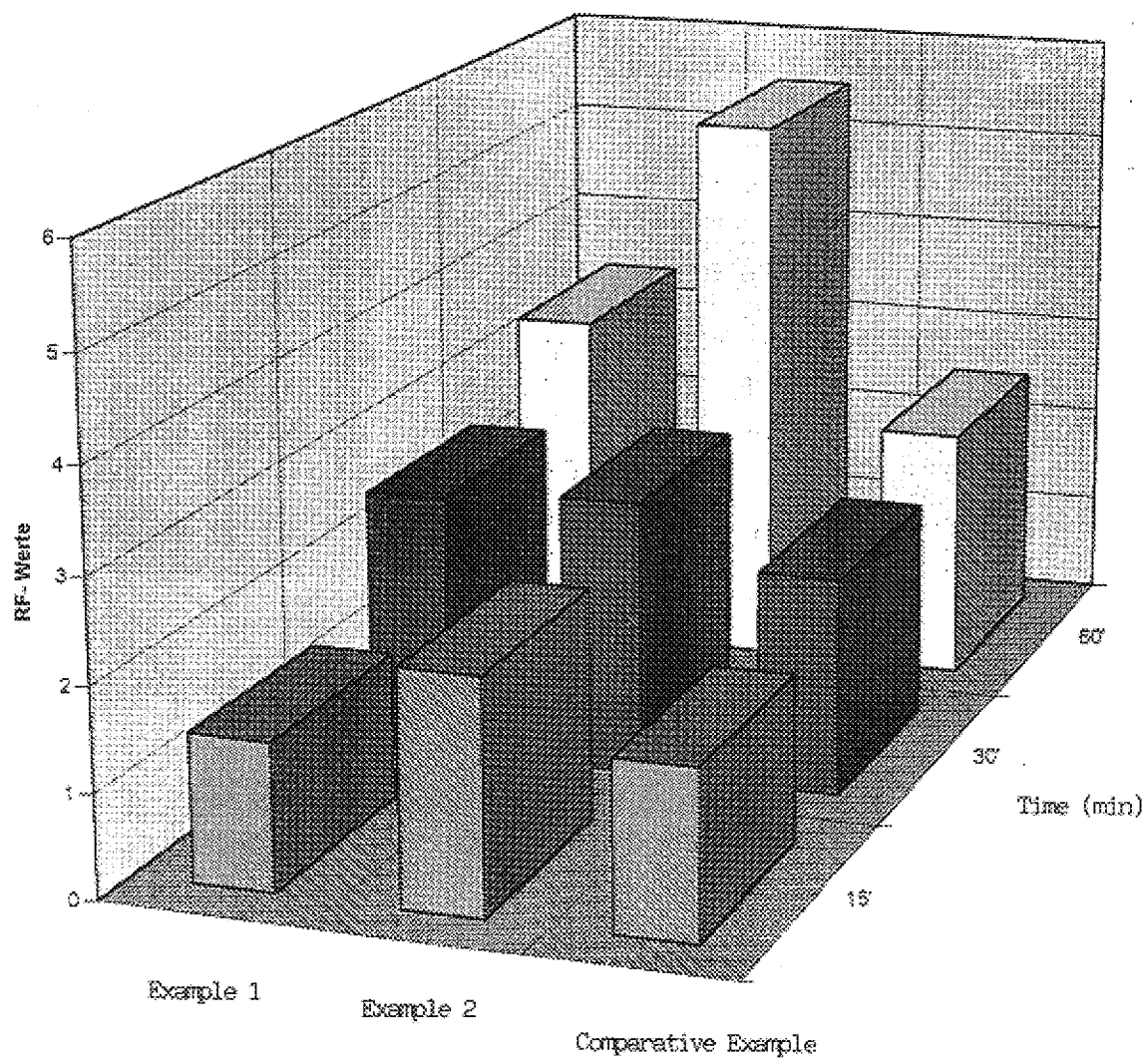

The present invention relates to the use of N,N'-substituted glycine and derivatives of glycine in disinfectants, in particular in aldehyde-free liquid disinfectants with activity against mycobacteria, which are particularly suitable for the disinfection of surfaces and instruments.

BACKGROUND OF THE INVENTION

Mycobacteria are still a great problem in the clinical area. Therefore, a tuberculocidal activity is demanded of disinfectants in this area in addition to a bactericidal, fungicidal and virucidal activity.

The trend in the field of surface and instrument disinfectants is increasingly in the direction of aldehyde-free preparations. On account of their toxicological properties and the odour problems which occur, aldehyde—containing disinfectants known in the prior art suffer from decreased user acceptance. Moreover, only a few biocides having tuberculocidal activity are known in the sector of aldehyde-free disinfectants.

These include, for example, N,N'-bis(3-amino-propyl) laurylamine from the amines group, which is employed in various surface and instrument disinfectants. As is known, formulations which have been prepared using this active compound have a raised pH. This leads to an increased risk in skin and material compatibility.

Of the aromatic alcohols which also have tuberculocidal activity, such as phenoxypropanols (e.g. 1-and 2-phenoxypropanol), markedly larger amounts must be employed in order to achieve a corresponding action. This leads to an increased risk of build-up of an undesired layer on the disinfected materials.

SUMMARY OF THE INVENTION

It was thus the object of the invention to make available disinfectants which have a good activity against mycobacteria, without having the abovementioned disadvantages.

Surprisingly, it has been found that, in addition to the activity against the bacterial spectrum known until now, N,N'-substituted glycine and N,N'-substituted derivatives of glycine are active against mycobacteria and, in particular in admixtures with cationic compounds, even act synergistically against mycobacteria.

The present invention thus relates to the use of an N,N'-substituted glycine and of derivatives of glycine (a) of the general formula I

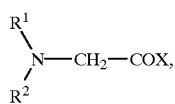

(I)

in which $R^1$ is hydrogen or a straight-chain or branched, saturated or unsaturated alkyl, alkaryl or aralkyl radical having 1 to 30 C atoms, which can optionally contain heteroatoms such as O, S and N, $R^2$ is a straight-chain or branched, saturated or unsaturated alkyl, alkaryl or aralkyl radical having 1 to 30 C atoms containing at least one primary, secondary or tertiary amino group and X is OH, $OR^3$, $NH_2$, $NHR^4$, $NR^4R^5$ or $O^-M^{30}$, where $R^3$, $R^4$ and $R^5$ are straight-chain or branched, saturated or unsaturated alkyl, alkaryl or aralkyl radicals which can be identical to or different from one another, and M is a metal cation, as active compound in a tuberculocidal disinfectant.

The present invention further relates to a tuberculocidal disinfectant, which is characterized in that it contains at least one N,N'-substituted glycine or derivative of glycine (a) in the form of the free acid or of a salt thereof, an ester or an amide of the above general formula I, where $R^1$, $R^2$, $R^3$, $R^4$, $R^5$ and X have the meanings indicated above, and at least one further active compound (b) selected from quaternary ammonium compounds, guanidinium derivatives, biguanides, aromatic alcohols and amines.

Preferred embodiments of the invention are the subject of the subclaims.

The tuberculocidal disinfectant is preferably aldehyde-free and is present as a liquid concentrate.

Preferably, $R^1$ is hydrogen and $R^2$ is an amino-substituted $C_2$- to $C_4$-alkyl radical, in particular an amino-substituted $C_3$-alkyl radical, preferably a 3-aminopropyl group which is substituted on the nitrogen atom by a radical R, where R is a $C_8$- to $C_{18}$-alkyl radical, in particular a $C_{10}$- to $C_{16}$-alkyl radical. Thus N-(3-aminopropyl)-N'-$C_{(8-18)}$-alkylglycine derivatives and N-(3-aminopropyl)-N'-$C_{(10-16)}$-alkylglycine derivatives are particularly preferred.

X is preferably OH. Thus $HOOC-CH_2-NH-(CH_2)_3-NH-R$, where R has the previously indicated meaning, is a preferred compound in the sense of the present invention.

The use according to the invention of the N,N'-substituted glycine or of the derivatives described above in the tuberculocidal disinfectant is preferably effected in combination with at least one further active compound (b) selected from quaternary ammonium compounds, guanidine derivatives, biguanides, aromatic alcohols and amines.

The tuberculocidal disinfectant according to the invention can contain 0.01 to 40% by weight, preferably 0.05 to 30% by weight and in particular 1 to 15% by weight of the N,N'-substituted glycine or its derivative (a) and, if it is used in combination with one of the abovementioned active compounds (b), optionally 1 to 70% by weight, preferably 5 to 60% by weight and in particular 10 to 30% by weight, of the active compound (b).

Use solutions having tuberculocidal activity can also be prepared which contain 0.1 to 10% by volume and in particular 0.2 to 5% by volume of the abovementioned concentrate.

The solvent used is preferably water or a water—containing solvent mixture. If a solvent mixture is employed, this preferably contains one or more alcohols having 2 to 4 C atoms, such as ethanol, 1-propanol, 2-propanol, n-butanol, isobutanol, sec-butanol or tert-butyl alcohol, in particular ethanol, i-propanol and/or 2-propanol.

For better wetting of the surfaces and for assisting the action, one or more surfactants can be added to the disinfectants according to the invention. As surfactants, certain anionic surfactants, for example soaps such as sodium stearate, potassium stearate or triethanolamine soaps, sulphonated aromatic hydrocarbons such as N-alkylbenzenesulphonates, sulphonated aliphatic hydrocarbons such as secondary alkanesulphonates, sulphonated olefins, sulphated fatty alcohols such as sodium lauryl sulphate, sulphated fatty alcohol ethers such as sodium lauryl polyglycol ether sulphate, sulphonated maleic acid esters such as lauryl sulphosuccinate, carboxymethylated fatty alcohol polyglycol ethers such as lauryl polyglycol ether acetate and/or non-ionic surfactants such as alkyl alkoxylates, alkylphenol ethoxylates, fatty acid ethoxylates, fatty acid alkylolamides, fatty acid alkylolamide ethoxylates, fatty amine ethoxylates, alkyl polyglycosides such as cocoylpolyglucose, laurylpolyglucose, decylpolyglucose or polyalkylene oxide block copolymers and/or amphoteric surfactants such as alkylaminoalkylglycines, betaines or sulphobetaines can preferably be used. Combinations of surfactants which are compatible with one another can also be employed.

In addition, complexing agents such as ethylenediaminetetraacetic acid, nitrilotriacetic acid or their salts, and sequestering agents such as phosphonobutanetricarboxylic acids can be added. To adjust the pH, organic acids such as citric acid, malic acid or lactic acid and/or inorganic acids such as, for example, hydrochloric acid, phosphoric acid or sulphuric acid can be used. To improve the material compatibilities, corrosion inhibitors, such as, for example, 1H-benzotriazole, tolyltriazole or mercaptobenzoxazole can be employed. Fragrances and colourants can furthermore be added.

The spectrum of action of the disinfectants according to the invention can be extended by addition of further active compounds (b). Compounds suitable for this are preferably quaternary ammonium compounds such as alkylbenzyldimethylammonium chloride, dialkyl-dimethyl-ammonium chloride, alkyldimethylethyl ethosulphate and/or dialkylmethyloxyethylammonium propionate, guanidinium derivatives such as coconut propylenediamineguanidinium diacetate, biguanides such as polyhexamethylene biguanide, furthermore aliphatic amines such as N,N'-bis(3-aminopropyl)dodecylamine and/or aromatic alcohols such as phenoxypropanols (e.g. 1-phenoxypropanol, 2-phenoxypropanol or mixtures thereof).

Use with quaternary ammonium compounds in the tuberculocidal disinfectant in this case leads to a synergistic action.

Formulations containing the N,N'-substituted derivatives of glycine according to the invention have a pH in the only slightly alkaline range, so that the risk of skin and material incompatibility is minimized. For example, for the commercial product Amphionic SFB from Rhône-Poulenc, which contains a mixture of N-(3-aminopropyl)-N'-C$_{(10-16)}$-alkylglycine derivatives, even use in hand cleansers is recommended by the manufacturer, although in concentrations which are markedly above those in the use solutions of the disinfectants according to the invention.

A preferred use of the disinfectants according to the invention is the disinfection of surfaces and instruments.

The following examples serve to illustrate the present invention.

EXAMPLES

In the following examples, the quantitative suspension test *Mycobacterium terrae* (ATCC 15755) according to DGHM [German Society for Hygiene and Microbiology, status at: Apr. 4, 1997) was used for testing the tuberculocidal action.

To assess the material compatibility, test samples of various plastics such as polycarbonate and floor coverings such as, for example, linoleum were tested according to the following process.

The appropriate test samples (50×50 mm with a varying thickness of up to a few mm) were inserted into the disinfectant use solutions according to the invention for 14 days at a temperature of 40° C. The weight difference (swelling) in % was then measured and a visual check of the test samples and the disinfectant solution was carried out.

Example 1

By mixing the appropriate constituents in a suitable vessel, a formulation (concentrate) was prepared which consisted of 10% by weight of N-(3-aminopropyl)-N'-C$_{(10-16)}$-alkylglycine derivatives (commercial product Amphionic SFB from Rhône-Poulenc), 10% by weight of tridecanepolyglycol ether with 12 ethylene oxide units and 80% by weight of water.

Example 2

As in Example 1, a formulation (concentrate) was prepared which consisted of 5% by weight of N-(3-aminopropyl)-N'-C$_{(10-16)}$-alkylglycine derivatives (commercial product Amphionic SFB from Rhône-Poulenc), 5% by weight of didecyldimethylammonium chloride, 10% by weight of tridecanepolyglycol ether having 12 ethylene oxide units and 80% by weight of water.

Example 3

As in Example 1, a formulation (concentrate) was prepared which consisted of 7.5% by weight of N-(3-aminopropyl)-N'-C$_{(10-16)}$-alkylglycine derivatives (commercial product Amphionic SFB from Rhône-Poulenc), 15% by weight of didecyldimethylammonium chloride, 5% by weight of phenoxypropanols, 10% by weight of tridecanepolyglycol ether having 12 ethylene oxide units and 62.5% by weight of water.

Example 4

As in Example 1, a formulation (concentrate) was prepared which consisted of 10% by weight of N-(3-aminopropyl)-N'-C$_{(10-16)}$-alkylglycine derivatives (commercial product Amphionic SFB from Rhône-Poulenc), 15% by weight of didecyldimethylammonium chloride, 10% by weight of phenoxypropanols, 10% by weight of tridecanepolyglycol ether having 12 ethylene oxide units and 55% by weight of water.

The concentrates from Example 1 and Example 2 were tested in a quantitative suspension test against *Mycobacterium terrae* (ATCC 15755) according to DGHM in comparison with a concentrate (Comparative Example 1), which instead of 10% by weight of N-(3-aminopropyl)-N'-C$_{(10-16)}$-alkylglycine derivatives as active compound contained 10% by weight of didecyldimethylammonium chloride and otherwise had the same composition as Example 1, in each case in the form of a use solution which contained 2% by volume of the respective concentrate. The logarithmic reduction factors were determined after a time of action of 15, 30 and 60 minutes. The results of this test are shown in Table 1 below or the diagram shown underneath.

TABLE 1

|  | Example 1 | Example 2 | Comparative Example 1 |
|---|---|---|---|
| 15' | 1.42 | 2.24 | 1.62 |
| 30' | 2.56 | 2.68 | 2.12 |
| 60' | 3.37 | 5.53 | 2.49 |

From of table 1 and the FIG. 1, it is seen from the values shown that the tuberculocidal action, in particular after a relatively long time of action, of the use solutions according to the invention exceeds that of the comparison solution (Comparative Example 1). Example 2 moreover illustrates the synergistic action on use in combination with a quaternary ammonium compound.

The concentrate from Example 3 was subjected to the material compatibility test described above in comparison with a formulation which instead of 7.5% by weight of N-(3-aminopropyl)-N'-C$_{(10-16)}$-alkylglycine derivatives contained the same amount of N,N'-bis(3-aminopropyl) laurylamine and was adjusted to the same pH (Comparative Example 2), in each case in the form of a use solution which contained 0.5% by volume of the respective concentrate. The results are shown in Table 2 below.

TABLE 2

| Materials tested | Example 3 | | Comparative Example 2 | |
|---|---|---|---|---|
| | Visual effect | Swelling | Visual effect | Swelling |
| Poly-carbonate | no sticking | none | distinct sticking | none |
| Linoleum, Marmorette 121–45 (Deutsche Linoleum Werke) | slight green discoloration | not tested | distinct green discoloration | not tested |
| Linoleum Marmorette 121–22 (Deutsche Linoleum Werke) | slight yellow discoloration | not tested | brown discoloration | not tested |

The concentrate from Example 4 was tested with respect to behaviour against polycarbonate in comparison with a formulation which instead of 10% by weight of N-(3-aminopropyl)-N'-C$_{(10-16)}$-alkylglycine derivatives contained the same amount of N,N'-bis(3-aminopropyl)laurylamine (Comparative example 3), in each case in the form of a use solution which contained 2% by volume of the respective concentrate. In the case of the concentrate according to the invention from Example 4, visual assessment showed only a slight clouding of the material, while the formulation from Comparative example 3 caused a severe sticking of the polycarbonate.

What is claimed is:

1. A method of disinfecting surfaces or instruments, which comprises: using on said surfaces or instruments an effective amount of an N, N' substituted derivative of glycine of the general formula (I):

R-NH-CH$_2$-CH$_2$-CH$_2$-NH-CH$_2$COX (I). 

2. The method according to claim 1, wherein R is a C$_{10}$ to C$_{16}$ alkyl radical.

3. The method according to claim 1, wherein at least one further active compound selected from the group consisting of quaternary ammonium compounds, guanidinium derivatives, biguanides, aromatic alcohols and amines is contained in the tuberculocidal disintectant.

4. The method according to claim 3, wherein the further active compound is selected from the group consisting of alkylbenzyldimethylammonium chloride, dialkyldimemthylammonium chloride, alkyldimethylethyl ethosulfate, dialkylmethyloxyethylammonium propionate, coconut proplylenediamineguanidinium diacetate, polyhexamethylene biguanide, N,N-bis (3-aminopropyl)-dodecylamine and phenoxypropanols.

5. The method according to claim 3, wherein the tuberculocidal disinfectant contains 0.01 to 40% by weight of the glycine derivative, and optionally 1 to 70% by weight of the further active compound.

6. The method according to claim 5, wherein the tuberculocidal disinfectant contains 0.05 to 30% by weight of the glycine derivative, and optionally 5 to 60% by weight of the further active compound.

7. The method according to claim 6, wherein the tuberculocidal disinfectant contains 1 to 15% by weight of the glycine derivative, and optionally 10 to 30% by weight of the further active compound.

8. The method according to claim 1, wherein the tuberculocidal disinfectant is present as a liquid concentrate.

9. The method according to claim 8, which comprises using the tuberculocidal disinfectant as a solution which contains 0.1 to 10% by volume of the concentrate.

10. The method according to claim 1, wherein the tuberculocidal disinfectant contains water or a water—containing mixture of water and at least one C$_2$ to C$_4$ alcohol, as a solvent.

11. The method according to claim 1, wherein the tuberculocidal disinfectant contains further additives selected from the group consisting of surfactants, complexing agents, and sequestering agents.

* * * * *